United States Patent [19]
Johnson et al.

[11] Patent Number: 5,846,929
[45] Date of Patent: Dec. 8, 1998

[54] PURIFICATION OF TYPE G BOTULINUM NEUROTOXIN AND PHARMACEUTICAL COMPOSITIONS THEREOF

[75] Inventors: Eric A. Johnson; Hiroshi Sugiyama; Carl J. Malizio, all of Madison, Wis.

[73] Assignee: Wisconsin Alumni Research Foundation, Madison, Wis.

[21] Appl. No.: 633,092

[22] Filed: Apr. 16, 1996

Related U.S. Application Data

[63] Continuation-in-part of Ser. No. 287,350, Aug. 8, 1994, abandoned.

[51] Int. Cl.$^6$ .............................. A61K 38/00; A23J 1/00; C12P 21/04
[52] U.S. Cl. ............................ 514/2; 514/21; 530/350; 530/412; 530/413; 530/416; 530/417; 530/418; 530/825; 435/68.1; 435/70.1; 435/70.3; 435/842
[58] Field of Search ......................... 514/2, 21; 530/350, 530/825, 412, 413, 416, 418, 417; 435/68.1, 70.1, 70.3, 842

[56] References Cited

PUBLICATIONS

Nukina et al, *Zbl. Bakt. Hyg.* A268, pp. 220–227, 1988.
Nukina et al, *FEMS Microbiology Letters*, vol. 79, pp. 165–170, 1991.
Girueuez et al, *Zbl. Bakt. Hyg.* A 262, pp. 179–188, 1986.
Ciccarelli et al, *Applied Environmental Microbiology*, vol. 34, No. 6, pp. 843–848, 1977.
Moberg, L.J. et al., Applied and Environmental Microbiology, vol. 35, No. 5, May 1978, pp. 878–880, "Affinity Chromatography Purification of Type A Botulinum Neurotoxin from Crystalline Toxic Complex".
Ciccarelli, A.S. et al., Applied Environmental Microbiology, vol. 34, No. 6, Dec. 1977, pp. 843–848, "Cultural and Physiological Characteristics of *Clostridium botulinum* Type G and the Susceptibility of Certain Animals to Its Toxin." Strain 89 of *Clostridium botulinum* type G, isolated by Gimenez and Ciccarelli in 1969, was characterized culturally, biochemically, and toxigenically.
Gimémez, J.A. et al., Zbl. Bakt. Hyg. A 262, (1986), pp. 179–188, "Molecular Characterization of a Protein, Insoluble at Low Temperature, Produced by *Clostridium botulinum* Type G".
Takeshi, K., Biol. Abstr. 83(7) AB–914, 68788 "Biochemical Properties of *Clostridium botulinum* Type G and *Clostridium hastiforme*."(1986).
Briozzo, J. et al., Applied and Environmental Microbiology, vol. 51, No. 4, Apr. 1986, pp. 844–848, "Effect of Water Activity and pH on Growth and Toxin Production by *Clostridium botulinum* Type G".
Nukina, M. et al., Zbl. Bakt. Hyg. A 268, 220–227 (1988), "Purification of *Clostridium botulinum* Type G Progenitor Toxin".
Nukina, M. et al., FEMS Microbiology Letters 79 (1991) 165–170, "Difficulties of molecular dissociation of *Clostridium botulinum* type G progenitor toxin".
Nukina, M. et al., FEMS Microbiology Letters 79 (1991) 159–164, "Detection of neutral sugars in purified type G botulinum progenitor toxin and the effects of some glycolytic enzymes on its molecular dissociation and oral toxicity".

*Primary Examiner*—Cecilia J. Tsang
*Assistant Examiner*—Abdel A. Mohamed
*Attorney, Agent, or Firm*—Quarles & Brady

[57] ABSTRACT

The isolation and purification of type G botulinum neurotoxin and complexes thereof is disclosed. Compositions containing the type G neurotoxin and the preparation of a type G toxoid are also disclosed.

4 Claims, No Drawings

PURIFICATION OF TYPE G BOTULINUM NEUROTOXIN AND PHARMACEUTICAL COMPOSITIONS THEREOF

RELATED CASES

The present application is a continuation-in-part of our earlier U.S. patent application Ser. No. 08/287,350 filed Aug. 8, 1994, now abandoned.

FIELD OF THE INVENTION

The present invention relates to botulinum toxin. More particularly, it relates to a method of purifying type G botulinum neurotoxin and novel pharmaceutical compositions containing type G botulinum neurotoxin.

BACKGROUND OF THE INVENTION

The most serious form of bacterial food poisoning is botulism which is caused by neurotoxins produced by *Clostridium botulinum*. The toxins are absorbed from the intestinal tract and transported via the circulatory system to motor nerve synapses where their action blocks normal neural transmissions. There are seven serotypes of the botulinum toxin with similar toxic activity but which differ antigenically. They are type A, B, C, D, E, F and G. Type A is the predominant toxin in cases of botulism in the United States, and type B toxin is most prevalent in Europe. The symptoms for the disease caused by the various serotypes are about the same, but the mechanism of action is different. It is possible to protect humans by a pentavalent immunization against types A to E, but because of unavailability of the purified toxin, specific antitoxins are not available for type G.

Crystalline botulinum toxin type A prepared in 1979 by E. J. Schantz of the Food Research Institute/Department of Food Microbiology and Toxicology, University of Wisconsin, Madison, Wis., has been used medicinally in the treatment of hyperactive muscle movement disorders, such as strabismus and other involuntary muscle disorders. Treatment involves injection of nanogram quantities (1 ng is equal to 30 mouse 50% lethal doses [30 U]) of the toxin directly into the hyperactive muscles. The toxin inhibits the release of acetylcholine from the motor neuron across the synaptic junction, causing a decrease in the hyperactivity of the injected muscles.

Botulinum toxin type A has become one of the most effective treatments for various types of dystonias, or involuntary muscle contractions, for many thousands of people. A major drawback to the use of botulinum toxin type A in the treatment of hyperactive muscle disorders in the development antibodies to the type A toxin resulting is ineffective treatment with the toxin, particularly for patients treated for spasmodic torticollis which requires larger and sometimes more frequent doses of the toxin by injection. The type A toxin is recognized by patient's immune systems as a foreign protein which stimulates antibody production. The fact that antibodies to the type A toxin have been formed in patients has been verified by the U.S. Center for Disease Control and other medical units.

Although the commercially available type A preparation is very useful, there is a need to have a pharmaceutical composition of a botulinum toxin of alternative serotype which can be used in patients who have developed antibodies to the type A toxin, and the many individuals who have antibodies to types A–E, including military soldiers and researchers who have been immunized with pentavalent toxoid.

There also is a need to have a purified type G botulinum neurotoxin which can be used to prepare a toxoid to protect against type G botulism as might occur naturally or in biological warfare. Nukina et al (12,13) have attempted to obtain a purified type G toxin; however, their products are highly unstable.

BRIEF SUMMARY OF THE INVENTION

It is an object of the present invention to disclose novel pharmaceutical compositions that contain type G botulinum neurotoxin and its protein complexes and which can be used in patients who have developed antibodies to the type A toxin.

It is a further object to disclose a novel method of purifying the type G neurotoxin from a natural source so that it can be used to prepare such pharmaceutical compositions and a toxoid that can be used to immunize patients against the type G botulism.

We have discovered a method of purifying type G botulinum neurotoxin from natural sources to obtain type G neurotoxin of high purity which can be used to prepare a toxoid or for medicinal use. Since type G botulinum neurotoxin has a different mechanism of action than type A it could be used in patients who have developed antibodies to the type A toxin or in individuals immunized with A–E pentavalent toxoid.

The novel method of purifying the type G botulinum neurotoxin basically comprises growing *C. botulinum* Type G under anaerobic conditions in a liquid medium culture containing trypticase-peptone and free of L-cysteine HCl precipitating the neurotoxin by adding yeast RNA and lowering the pH to about 3.4 with acid; extracting the toxin from the precipitate with a phosphate-NaCl buffer (pH7); centrifuging the mixture and dissolving the precipitate in phosphate buffer (pH 6.0); adding RNAase and incubating the mixture at 37° C., to salt out the toxin as a precipitate; suspending the precipitated toxin in sodium citrate buffer (pH 5.5) and loading it on a DEAE-Sephadex A-50 gel; collecting the $A_{260}/A_{278}$ fractions with a ratio of 0.6 or less; salting out the toxin; loading it on a SP-Sephadex column; eluting the neurotoxin-containing fractions and then purifying the neurotoxin by PAPTG affinity chromatography to obtain a stable, highly purified type G neurotoxin molecule weighing 144,000 daltons. The type G toxin can be activated by treatment with a protease such as Endoproteinase Lys-C. Purified, activated type G toxin has a specific activity of greater than $1 \times 10^7$ $LD_{50}$/mg protein and is greater than 90% pure by SDS-PAGE.

The novel pharmaceutical compositions of the present invention are lyophilized products which contain about $10^5$ to $5 \times 10^7$ mouse $LD_{50}$'s (U) per mg of protein of active botulinum neurotoxin type G.

At the time of use, the compositions can be diluted to the desired concentration by aseptically adding physiological saline or buffers to obtain a solution suitable for injection. The desired amount of the solution (e.g. 0.1 ml) is then injected using a suitable needle, such as an electromyographic needle, into the proper or hyperactive muscle.

DESCRIPTION OF THE PREFERRED EMBODIMENT

The preferred embodiment of the compositions of the present invention is a lyophilized product containing type G botulinum neurotoxin or its protein complex containing $10^5$ to $5 \times 10^7$ U of activity dependent upon the degree of purification. The lyophilized product may be prepared from a prelyophilization formulation containing organic or inorganic buffers of appropriate pH and ionic strength. The toxin can also be stabilized by the addition of exogenous proteins (e.g. serum albumin) and other materials (e.g. trehalose).

The preferred method of preparing the compositions of the present invention comprises dissolving the purified botulinum type G toxin with a solubilizing amount of sodium phosphate buffer or other appropriate buffer (pH 6.2–7.4) and ultrafiltering the solution to maintain sterility. It is then dried by lyophilization for dispensing to physicians.

Type G botulinum complexes and purified neurotoxin of the present invention are produced under anaerobic conditions in liquid medium culture. The neurotoxin component has a molecular weight of 140–150 kda as determined by SDS-PAGE. Its activity is increased by treatment with Endoproteinase Lys-C. The type G toxin produced from *Clostridium botulinum* type G has a specific $LD_{50}$ per mg. toxicity in mice of $>1 \times 10^7$ U/mg, an $A_{260}/A_{278}$ ratio of less than 0.60, and a distinct pattern of banding on gel electrophoresis. The neurotoxin also can be isolated as complexes of 300–500 kDa ($10^5$ to $10^7$ U/mg) which are more stable than the purified neurotoxin and may have even greater utility in medicine.

For lyophilization, aliquots (usually 0.1 ml) of the toxin solutions can be pipetted into 0.5 dram (ca. 1.85-ml), screw-cap glass vials with rubber-lined closures. The solutions in glass vials may then be frozen in a bath of liquid nitrogen at $-200°$ C. or by placing them in a freezer at $-20°$ C. or $-70°$ C. The loosely capped vials can then be placed into a 150 ml lyophilization flask that had been precooled in liquid nitrogen. The lyophilization flask is partially immersed in liquid nitrogen and connected to a lyophilizer (Virtis Freezemobile 12, Virtis Co., Inc. Gardiner, N.Y.). The liquid nitrogen is maintained in contact with the lyophilization flask until the pressure drops to approximately 30 millitors (ca. 4.0 kPa). The liquid nitrogen jacket is then removed, the flask and contents are allowed to come to room temperature (ca. 3 to 4 h), and the drying procedure is continued for 12 to 18 h. The pressure is maintained at or below 20 millitorrs for the remainder of the cycle. Condenser temperature on the lyophilizer is kept constant at ca. $-60°$ C. After the drying cycle is completed, the lyophilized toxin vials are removed from the flask, tightly capped, and held at room temperature for up to 3 days until the mouse assay. The lyophilized preparations can be reconstituted in 1.0 ml of distilled water or 0.85% saline as a diluent.

MATERIALS AND METHODS

I. Toxin Complex Production

*C. botulinum* Type G strain 89 (available from CDC, Atlanta Ga.) was initially obtained from a soil sample from Mendoza, Argentina. Long term storage is in cooked meat medium (Difco). Working stocks were stored in a medium (TPGY) containing 5% trypticase-peptone (BBL), 0.5% Bacto-peptone (Difco), 2% yeast extract (Difco), 0.4% glucose (Mallinckrodt), and 0.2% L-cysteine HCl (Sigma) adjusted to pH 7.3. An 8% final concentration of sterile glycerol was added to 16 to 40 hour cultures as a cryoprotectant. Cultures were stored at $-60°$ to $-80°$ C.

The toxin production medium was free of L-cysteine HCl and contained 2.0% trypticase-peptone (BBL), 1.0% proteose-peptone (Difco), 0.5% yeast extract (Difco), and 0.5% glucose (Mallinckrodt) adjusted to pH 7.3 (2). The cysteine HCl was omitted because we discovered that it caused cell clumping and reduced the yield of toxin. When large volumes were used, a 14% glucose solution was autoclaved for 20 minutes and added to the large volume which was separately autoclaved for 1 hour.

After thawing, a working stock culture was mixed and 0.1–0.2 ml inoculated into a 10 ml tube of TPGY and incubated under anaerobic conditions at 30° C. After 16–40 hours incubation, 10 ml of TPGY were inoculated into 100 ml of toxin production medium. After 16 hour incubation, 100 ml were inoculated into 1400 ml of toxin production medium. Finally after 16 hours incubation, 1400 ml were inoculated into 14 liters of toxin production medium in 20 liter carboys. The carboys were incubated 6 days at 30° C. To maintain anaerobic conditions a 10% $CO_2$+90% $N_2$ gas mixture filtered through a 0.2 um filter (Gilman) was bubbled through a gas dispersion tube into the toxin production medium contained in a 20 liter carboy for 3–4 hours prior to inoculation and during the entire 6 day incubation. Exhaust from carboy was bubbled through gas dispersion tubes into two side arm flasks connected in series containing 5.25% hypochlorite. (This method gave toxin titers in the culture fluid of $>3.0 \times 10^4 LD_{50}$/ml compared to the $1.3 \times 10^4 LD_{50}$/ml obtained by Nukina et al (12), who did not use anaerobic conditions, used a different strain, and used a cysteine containing culture medium.)

Toxin purification

All buffers except acetate were made by titrations of equimolar solutions of basic and acidic components. Acetate buffer was made by addition of NaOH solution to the desired molarity of acetic acid. All chromatography was done at room temperature.

The toxin in the culture fluid was precipitated by adding 0.2 g/liter RNA (Sigma) and lowering the pH to 3.4 with 3M HCl or sulfuric acid. The addition of RNA prior to acidification made it possible to recover all of the toxin from the culture fluid. (Nukina et al (12) used 4N sulfuric acid and no RNA.) The acidified culture fluid was stored 16–72 hours at 4° C.

The toxin was extracted from the precipitate with 0.2M phosphate +0.5M NaCl buffer, pH 7.0 for two hours at room temperature. The extract was centrifuged and the clarified supernatant fluid saved as the first extract. The pellet was reextracted in the same buffer for 1 hour at room temperature and then centrifuged. The clarified supernatant fluid obtained was combined with the first extract fluid and made to 60% saturation with $(NH_4)_2SO_4$ (39 g /100 ml) before being stored at 4° C. (Nukina et al (12) used a different extraction buffer which lacked sodium chloride and they treated their precipitate by sonication to release toxin.) The salted out precipitate of the extraction was collected by centrifugation and dissolved in 100 ml of 0.05M phosphate buffer pH 6.0. The toxin solution was incubated at 37° C. for three hours after adding 0.05 mg/ml RNase (Sigma type 1A). This step removes the RNA associated with the toxin complex. The toxin solution was then made with 60% $(NH_4)_2SO_4$(39 g/100 ml) and stored at 4° C. (In contrast, in the Nukina et al procedure, the acid precipitated extract and residual extract are then trypsinized which we have discovered results in a less stable neurotoxin molecule. Instead of trypsin, we use Endo-proteinase Lys-C at a later step in our process because it acts only at the lysine residue.)

DEAE-Sephadex chromatography. The salted out precipitate of RNase treated material was collected by centrifugation, suspended in 40 ml of 0.05M sodium citrate buffer, pH 5.5. The toxin sample was loaded on a DEAE-Sephadex A-50 gel (Sigma) that had been equilibrated and washed with citrate buffer. The toxin did not bind under these conditions and the toxin was washed out of the column with citrate buffer. The toxin came off in the first large protein peak. Fractions with $A_{260}/A_{278}$ ratio of 0.6 or less were pooled and made saturated with 60% $(NH_4)_2SO_4$ as DEAE-toxin. The toxin had a specific activity of $1.9 \times 10^6$ $LD_{50}$/mg protein with a recovery of greater than 90%.

(Nukina et al, use several different steps: 1) Gel filtration on Sephadex G-200 column; 2) Protamine treatment and SP-Sephadex percolation; 3) SP-Sephadex chromatography; and 4) Second gel filtration on Sephadex G-200. The specific activity of the resulting material is $1.9 \times 10^6$ $LD_{50}$/mg protein with a recovery of 39%. As described above, we do not use these extra purification steps and we end up with a higher yield of toxin complex.)

SP-Sephadex chromatography. The pool containing the salted out toxin complex was collected by centrifugation and resuspended in 0.02M acetate buffer, pH 6.0. The sample was dialyzed against three changes of the acetate buffer over 2 to 3 days at 4° C. During this dialysis a precipitate formed and was removed by centrifugation. The soluble toxin in the supernatent was loaded on a SP-Sephadex C-50 column equilibrated and washed with the acetate buffer. The column was eluted with a gradient of 0 to 0.5M NaCl in the acetate buffer. The toxin eluted in two separate peaks. The first peak came off the column unretarded and contained 40–60% of the recovered toxin. The second peak eluted with 0.25M NaCl and also contained approximately 50% of the recovered protein. The toxin pools were not combined. The second peak was precipitated with 60% $(NH_4)_2SO_4$ and stored at 4° C. The toxin in this peak had a specific toxicity of $6 \times 10^6$ $LD_{50}$/mg protein. (Nukina et al did not generate two toxin fractions in their purification procedure.)

II. Purification of the Neurotoxin Molecule. It is important to realize that the neurotoxin component has distinct properties from the toxin complex. It has a different molecular size, it is less stable compared to the toxin complex, and is entirely responsible for the toxicity.

PAPTG affinity chromatography. The toxin fraction that eluted in the NaCl gradient from the SP-Sephadex column was collected, centrifuged and suspended in 0.02M acetate, pH 6.0. It was dialyzed at 4° C. against three changes of 0.02M acetate buffer, pH 6.0, for 48 hours. The sample was centrifuged to remove any precipitate that formed. The toxin was loaded onto PAPTG gel (affinity gel), using a modified procedure of Moberg and Sugiyama (11) except that 0.02M acetate (pH 6.0) was used in place of 0.025M phosphate buffer (pH 6.3). The toxin and affinity gel was mixed with gentle turning for 2 hours at room temperature, washed on a splintered glass filter with 100 ml of 0.02M acetate pH 6.0 and then washed with 100 ml of 0.1M tris buffer, pH 7.9. The gel was then collected and loaded on a column in 0.1M tris buffer, pH 7.9 and washed with 15 ml of loading buffer. The column was then washed with 15 ml of the tris buffer +0.05M NaCl. The toxin was then eluted with the tris buffer +0.5M NaCl.

The neurotoxin molecule that eluted from the PAPTG gel had a specific activity of $>1 \times 10^7$ $LD_{50}$/mg protein after activation with Endoproteinase Lys-C.

The neurotoxin was stable in the elution buffer for 14 days at 4° C. (the longest time period tested) and for several months as an ammonium sulfate precipitate. The purified neurotoxin had a molecular weight of 144,000 daltons as determined by gel filtration and gave a single band with a molecular weight of ~145,000 during analysis by SDS-PAGE. The yield of neurotoxin ranged from 9 to 11%. (In contrast, the neurotoxin isolated by Nukina et al. had a specific toxicity $4 \times 10^6$ $LD_{50}$/mg protein (13). Their toxin was unstable and lost activity within a two hour time period (13). Their recovery was only about 0.1% and Nukina et al. concluded that this may reflect the extreme lability of their type G toxin component. Pages 169 and 170.)

SDS-PAGE. The results of the purification process were analyzed by SDS-PAGE using the Phastsystem (Pharmacia) with 10–15% acrylamide gradient slab gels (sample load per well was 2 to 4 ug protein/4 ul). Gels were run and stained with Coomassie blue according to the Phastsystem manual with the exception that sample buffer did not contain reducing agent. 4% 2-mercaptoethanol was added to samples when S—S bond reduction was desired.

Electrophoresis and electroblotting. Gels for blotting were made and electrophoresis and electroblotting were preformed as described previously (7).

Amino acid sequence. The toxin was partially sequenced using pulsed-liquid phase (model 477-A) Applied Biosystems protein sequencers. The sequence confirmed its uniqueness compared to other botulinum neurotoxins.

Protein assays. Protein was determined by BIO-RAD method (BIO-RAD Lab., Richmond, Calif.) with standards of serum albumin. Protein was also estimated spectrophotometrically assuming an $A_{278}$ of 1.85 for a 1.0 mg/ml solution.

Activation of Toxin. Endoproteinase Lys-C (Sigma) (5U/mg) was used to activate purified toxin solutions (7,9). Activation was done at pH 6.0 to 7.9 for 1 hour at 37° C. The reaction was stopped by addition of TLCK (sigma) at 10 times the enzyme weight.

Toxicity assays. Toxicity was determined in mice of 18–25 grams. A standard curve was plotted of the log of intraperitoneal (IP) $LD_{50}$ vs the log of minutes to death intravenously (3). IP toxicity was determined by injecting (0.5 ml) of two fold serial diluted samples into separate groups of five mice. Dilutions were in 0.03M phosphate buffer +0.2% gelatin, pH 6.3. Deaths were recorded for four days and $LD_{50}$ determined as previously described (15). IV injections (0.1 ml) were made into groups of three mice and an average time to death determined for each concentration.

Molecular weight. Toxic fractions off SP-Sephadex C-50 and PAPTG chromatography were gel filtered on a Superose 6 column (Pharmacia).

Samples were dissolved in 1 ml of 0.075M phosphate buffer +0.5M NaCl, pH 7.9. The column was run at pH 7.9 to prevent simple charge interactions that may occur at an acidic pH.

The column was calibrated with thyroglobulin (molecular weight 669,000), ferritin (440,000), catalase (232,000), and aldolase (158,000) from the high molecular weight calibration kit (Pharmacia)(1).

RESULTS

Toxin production. The strain, methods and medium used in these experiments produced 3 to $4 \times 10^4$ $LD_{50}$/ml in the culture fluid.

Purification. The addition of RNA resulted in all the toxin complex consistently precipitating and did not interfere with the purification. A sample purified by precipitation with acid only gave similar results on SDS-PAGE, but the yield was 75% lower.

The toxin loaded to SP-Sephadex C-50 was split into two toxic peaks. The first peak that came through the column unretarded consisted of the toxin molecule and other proteins of similar weight. This toxin peak represented 22% of total toxicity loaded. The toxin in this peak was purified to a bimolecular complex on the PAPTG affinity column. The bimolecular complex could not be broken without dissociation of the toxin molecule and loss of activity.

The second peak eluted from the SP-Sephadex column with 0.25M NaCl. It contained 35% of total toxicity loaded.

When this material was eluted from the PAPTG gel after a sequence of washes, it contained only the neurotoxin molecule and it had a specific activity of greater than $1.0 \times 10^7$ $LD_{50}$/mg protein. The toxin off the PAPTG column was stable in the elution buffer for up to 14 days. This was the longest period tested.

Amino acid sequence. The partial amino acid sequences obtained (16 for the light chain and 13 for the heavy chain) showed greatest homology to type B toxin with 11 out of 16 AA being the same in the light chain and 6 out of 13 being the same in the heavy chain. This homology, only about 60%, confirms that the G toxin is unique among the botulinum neurotoxins. Type A toxin matched 8 of 16 in the light chain and 6 of 13 in the heavy chain. The partial sequences obtained by amino acid sequencing of the G toxin are in 100% agreement for the light chain and 73% agreement for the heavy chain with those obtained by the DNA sequence (10). Further amino acid sequencing was blocked by an unknown structure. The light chain sequence was used to make a probe to identify the location of the DNA sequence.

Activation. Samples off the PAPTG column were best activated with 5U of Endoproteinase Lys-C/mg protein generally giving 20 to 100 fold activation. These results were the same for pH 6.0, 7.0, 7.9. Activation of samples off the PAPTG column with trypsin resulted in the nicking of a 10,000 to 15,000 molecular weight peptide off of the heavy chain. Activation with 5U Endoproteinase Lys-C resulted in all toxin being nicked. This material had the best activity and produced a heavy chain (approximately 100,000 molecular weight) and a light chain (approximately 50,000 molecular weight) similar in size to Type A or B botulinum toxin chains on SDS-PAGE under reducing conditions.

The purified toxin had a specific toxicity of $>1.0 \times 10^7$ $LD_{50}$/mg protein which, in conjunction with SDS-PAGE, indicates that the toxin is highly purified. Affinity chromatography and the pH-dependent association of the large protein complex were used to bind the neurotoxin and dissociate it. At pH 7.9 the complex dissociated and the neurotoxin was eluted by a higher NaCl concentration than the contaminants. The total activation of the toxin by Endoproteinase Lys-C was also responsible for the high specific toxicity.

The following Examples further illustrate the present invention.

EXAMPLE 1

A pharmaceutical composition suitable for injection is prepared from a liquid formulation which contain 100 U type G neurotoxin and 0.5 mg HSA stabilizing protein, pH 6.4 to 6.6, in 1 ml of sterile water in a vial. The formulation is lyophilized to obtain a lyophilized solid which can be reconstituted with water or saline prior to use.

EXAMPLE 2

Botulinum neurotoxin type G paralyzing ability was tested in a rabbit ptosis model which showed that it had paralytic activity. These results showed that it can be used in humans for treating hyperactive muscle disease and that it can be used where type A is ineffective. Antitoxins to botulinum serotypes A–F do not neutralize type G botulinum toxin activity.

EXAMPLE 3

A safe and effective amount of the reconstituted composition of Example 1 is administered to a patient in which types A–F botulinum toxin are no longer effective to treat a hyperactive muscle disease and the hyperactive muscle disease condition is improved.

EXAMPLE 4

A toxoid for type G botulinum toxin is prepared by treating the active type G neurotoxin with a dilute solution of formalin (0.1–0.5%) for several days at room temperature. On injection good titers of antibodies are formed in rabbits, horses, monkeys and humans.

While the exact dose of the purified type G botulinum neurotoxin to be administered varies with the size of the patient and the condition to be treated the dosage will normally range from about 1 U to about 300 U.

Type G neurotoxin associates with different proteins to form two types of complexes. The first type, a bimolecular complex does not separate at alkaline pH as other serotypes of botulinum toxin do. Breaking this complex results in an unstable protein that dissociates and quickly looses activity (Nukina et al method). In the second type of complex, the neurotoxin is associated with uncharacterized proteins. In the process of the present invention, we separate the two types of complexes and purify the neurotoxin molecule present in the second complex to obtain a protein with a MW of approximately 144,000 daltons. The neurotoxin has a specific activity of greater than $1.0 \times 10^7$ $LD_{50}$/mg protein and is greater then 90% pure by SDS-PAGE. Our process results in a stable, highly purified, neurotoxin molecule with retention of activity. No other investigators have obtained a type G toxin of equal toxicity and stability. Stability is critical for medical use of the neurotoxin and our process is the only known process that provides a stable neurotoxin molecule.

It will be apparent to those skilled in the art that there are significant difference between the products and processes of the present invention and those of Nukina et al (12,13).

The main differences are as follows:

(1) We use a different bacterial strain.

(2) We use a different culture medium.

(3) We use a different culturing method by omitting cysteine and continually sparging with an anaerobic gas mixture.

(4) Nukina et al. trypsinize the entire culture extract. The resulting toxin product was unstable.

(5) Our purification procedure is completely different from that of Nukina et al.

(6) We isolate a different toxin complex than do Nukina et al.

(7) Pure neurotoxin is obtained from the complex by a different procedure which includes affinity chromatography.

(8) The resulting pure neurotoxin has a much higher specific toxicity and is stable whereas the Nukina et al. product decays in hours.

It also will be apparent to those skilled in the art that a number of modifications and changes can be made without departing from the spirit and scope of the present invention. Therefore, it is intended that the invention only be limited by the claims.

REFERENCES

1. Andrews, P. 1964. The gel-filtration behavior of proteins related to their molecular weights over a wide range. J. Biochem. 96:596–606.

2. Briozzo, J., E. A. Delagarde., J. Chirife, and J. L. Parada. 1986. Effect of water activity and pH on growth and toxin production of *Clostridium botulinum* type G. Appl. Environ. Microbiol. 51:844–848.
3. Boroff, D. A., and U. Fleck. 1966. Statistical analysis of a rapid in vivo method for the titration of the toxin of *Clostridium botulinum*. J. Bacteriol. 92:1580–1581.
4. Campbell, K., M. D. Collins., and A. K. East. 1993. Nucleotide sequence of the gene coding for *Clostridium botulinum* (*Clostridium argentinense*) type G neurotoxin: genealogical comparison with other clostridium neurotoxins. Biochem et Biophys Acta. In Press.
5. Ciccarelli, A. S., D. N. Whaley, L. M. McCroskey, D. F. Gimenez, V. R. Dowell, and C. L. Hatheway. 1977. Cultural and physiological characteristics of *Clostridium botulinum* type G. Appl. Environ. Microbiol. 34:843–848.
6. Gimenez, J. A., O. Cascone., M. J. Biscoglio., D. Bonino., and A. C. Biscoglio. 1986. Molecular characterization of a protein, insoluble at low temperature, produced by *Clostridium botulinum* type G. Zbl. Bakt. Hyg. A262:179–188.
7. Gimenez, J. A., and B. R. DasGupta. 1990. Botulinum neurotoxin type E fragmented with Endoproteinase Lys-C Reveals the site trypsin nicks and homology with tetanus neurotoxin. Biochimie 72:213–217. Matsudaira, P. 1978. Sequence from picomole quantities of proteins electroblotted onto polyvinylidene difluoride membranes. J. Biol. Chem. 262, 10035–10038.
8. Gimenez, J. A., and H. Sugiyama. 1987. Simplified purification method for *Clostridium botulinum* type E toxin. Appl. Environ. Microbiol. 53:2827–2830.
9. Kozaki, S., Y. Oga., Y. Kamata., and G. Sakaguchi. 1985. Activation of *Clostridium botulinum* type B and E derivative toxins with Lysine-specific proteases. FEMS Micro. Lett. 27:149–154.
10. Lewis S. E., S. Kulinski., D. Reichard., and J. Metzger. 1981. Detection of *Clostridium botulinum* type G toxin by enzyme-linked immunosorbent assay. Appl. Environ. Microbiol. 42:1018–1022.
11. Moberg, L. J., and H. Sugiyama. 1977. Affinity chromatography purification of type A botulinum neurotoxin from crystalline toxic complex. Appl. Environ. Microbiol. 35:878–880.
12. Nukina, M., Y. Mochida., S. Sakaguchi., and G Sakaguchi. 1988. Purification of *Clostridium botulinum* type G progenitor toxin. Zbl. Bakt. Hyg. A268:220–227.
13. Nukina, M., Y. Mochida., S. Sakaguchi., and G Sakaguchi. 1991. Difficulties of molecular dissociation of *Clostridium botulinum* type G progenitor toxin. FEMS Micro. Lett. 79:165–170.
14. Nukina, M., T. Miyata., S. Sakaguchi., and G. Sakaguchi. 1991. Detection of neutral sugars in purified type G botulinum progenitor toxin and the effects of some glycolytic enzymes on its molecular dissociation and oral toxicity. FEMS Micro. Lett. 79:159–164.
15. Reed, L. J., and H. Muench. 1938. A simple method of estimating fifty percent endpoints. Amer. J. Hyg. 27:493–497.

We claim:

1. A type G botulinum neurotoxin having a molecular weight of about 144,000 daltons as determined by gel filtration and SDS-PAGE, said neurotoxin having a specific toxicity of between $1.0 \times 10^7$ and $5.0 \times 10^7$ $LD_{50}$/mg protein wherein the neurotoxin was obtained from *Clostridium botulinum* grown under anaerobic conditions.

2. A method of obtaining natural type G botulinum neurotoxin which comprises (a) growing *Clostridium botulinum* strain 89 under anaerobic conditions in a suitable medium to obtain a culture broth having activity of between $3.0 \times 10^4$ and $4.0 \times 10^4$ $LD_{50}$/ml; and, (b) isolating the neurotoxin by adding yeast RNA and adjusting pH of the broth to about 3.4 to precipitate a toxin complex, adding RNAase and treating the precipitated toxin by DEAE Sephadex ion exchange purification and PAPTG affinity chromatography to obtain the isolated neurotoxin, wherein yield of the neurotoxin is between 9% and 11%.

3. A method of claim 2 in which the neurotoxin is activated with Endoproteinase Lys-C.

4. A method of obtaining type G botulinum neurotoxin which comprises (a) growing *Clostridium botulinum* under anaerobic conditions in a suitable medium to obtain a culture broth having activity of $>3.0 \times 10^4$ and $4.0 \times 10^4$ $LD_{50}$/ml; and, (b) isolating the neurotoxin by adding yeast RNA and adjusting pH of the broth to precipitate a toxin complex, adding RNAse and treating the precipitated toxin by ion exchange purification and affinity chromatography to obtain the isolated neurotoxin, wherein yield of the neurotoxin is between 9% and 11%.

* * * * *

UNITED STATES PATENT AND TRADEMARK OFFICE
CERTIFICATE OF CORRECTION

PATENT NO. : 5,846,929
DATED : December 8, 1998
INVENTOR(S) : Eric A. Johnson, et al.

It is certified that error appears in the above-identified patent and that said Letters Patent is hereby corrected as shown below:

In the Claims: Claim 4, line 5, please replace [>] with between.

Column 4, Line 12:
"$CO_2+90\%$" should be --$CO_2+90\%$--

Column 6, Line 26:
"(sigma)" should be --(Sigma)--

Signed and Sealed this

Twenty-second Day of June, 1999

Attest:

Q. TODD DICKINSON

Attesting Officer      Acting Commissioner of Patents and Trademarks